United States Patent [19]

Herzberg et al.

[11] Patent Number: 5,352,785

[45] Date of Patent: Oct. 4, 1994

[54] CONTINUOUS PROCESS FOR PURIFYING PERFLUOROCHEMICAL COMPOSITIONS

[75] Inventors: Thomas C. Herzberg, Afton Township, Washington County; Robert B. Fletcher, St. Paul; Randall F. Henderson, Cottage Grove, all of Minn.

[73] Assignee: Minnesota Mining and Manufacturing Company, St. Paul, Minn.

[21] Appl. No.: 39,861

[22] Filed: Mar. 30, 1993

[51] Int. Cl.$^5$ .................. C07D 265/00; C07C 209/84; C07C 41/34; C07C 17/38
[52] U.S. Cl. ..................... 544/178; 544/106; 549/511; 564/497; 564/498; 564/510; 564/2; 568/580; 568/581; 568/682; 568/19; 568/24; 568/65; 570/118; 570/134; 570/177
[58] Field of Search .............. 568/580, 19, 581, 682, 568/24, 65; 570/118, 134, 177; 564/2, 497, 498, 510; 544/106, 178; 549/511

[56] References Cited

U.S. PATENT DOCUMENTS

| | | | |
|---|---|---|---|
| 3,737,470 | 6/1973 | Cottle | 260/653 |
| 4,029,552 | 6/1977 | Fozzard | 203/69 |
| 4,035,250 | 7/1977 | Walters et al. | 204/59 F |
| 4,618,731 | 10/1986 | Beck | 568/842 |
| 4,766,261 | 8/1988 | Bierl | 570/179 |
| 4,929,317 | 5/1990 | Nishimura et al. | 204/59 R |
| 5,093,432 | 3/1992 | Bierschenk et al. | 525/331.6 |

FOREIGN PATENT DOCUMENTS

| | | | |
|---|---|---|---|
| 2-412800 | 8/1992 | Japan | C07B 39/00 |
| WO90/06296 | 6/1990 | PCT Int'l Appl. | C07B 39/00 |

OTHER PUBLICATIONS

Arcus et al., *Testing for Chemical Inertness in Electronic Coolants*, Int. Electronic Circuit Packaging Symposium, 10th Symposium, paper 2/4, 1969.

R. J. Kaufman, "Medical Oxygen Transport Using Perfluorochemicals," *Biotechnology of Blood*, edited by J. Goldstein, Chapter 7, pp. 127–162, Butterworth-Heinemann, Stoneham, Mass. (1991).

Kirk-Othmer *Encyclopedia of Chemical Technology*, Third Edition, vol. 10, pp. 874–881 (especially, p. 878), John Wiley & Sons, New York (1980).

Moore et al., J. Fluorine Chem. 32, 41 (1986).

Nishimura et al., J. Printed Circuitry 6 (4), 203 (1991).

*Primary Examiner*—Johann Richter
*Assistant Examiner*—Margaret J. Page
*Attorney, Agent, or Firm*—Gary L. Griswold; Walter N. Kirn; Lucy C. Weiss

[57] ABSTRACT

A process for the purification of a perfluorochemical composition comprises continuously mixing the perfluorochemical composition, comprising a liquid mixture of inert perfluorochemicals (e.g., perfluoroalkanes, perfluoroethers, perfluoroaminoethers, or perfluoroalkyl tertiary amines) and isomeric fluorohydrochemicals, with a stabilization composition comprising water-miscible alkanol and an aqueous solution of base (such as potassium hydroxide) made by dissolving the base in an amount of water sufficient to dissolve or disperse the fluoride salt by-products of the subsequent reaction of the base with the fluorohydrochemicals to form fluoroolefins, the amount of the alkanol in the stabilization composition being in stoichiometric excess of the amount needed to completely convert the fluoroolefins to alkoxyvinyl ethers. The process can be utilized to purify the product mixtures resulting from fluorination methods such as direct fluorination or ECF.

20 Claims, No Drawings

CONTINUOUS PROCESS FOR PURIFYING PERFLUOROCHEMICAL COMPOSITIONS

This invention relates to a process for the purification of perfluorochemical compositions, namely, a process for the separation and, optionally, recovery of substantially inert perfluorochemicals from a mixture of inert perfluorochemicals and isomeric fluorohydrochemicals.

Perfluorochemicals such as perfluoroalkanes, perfluoroethers, and perfluoroalkyl tertiary amines are known to be essentially chemically inert. This inertness contributes to their suitability for numerous industrial uses, e.g., as heat transfer and test-bath fluids, hydraulic fluids, and lubricants. In addition, many inert perfluorochemicals (and emulsions and dispersions thereof) are capable of dissolving, transporting, and delivering biologically and chemically significant quantities of oxygen, and this capability renders such perfluorochemicals useful as components of "blood substitutes," which can be employed in the treatment of heart attack, stroke, and other vascular obstructions, and as adjuvants to coronary angioplasty, cancer radiation treatment, and chemotherapy. (See, e.g., R. J. Kaufman, "Medical Oxygen Transport Using Perfluorochemicals," *Biotechnology of Blood*, edited by J. Goldstein, Chapter 7, pages 127-62, Butterworth-Heinemann, Stoneham, Mass. (1991).)

Inert perfluorochemicals can be prepared by electrochemical fluorination (ECF), in which an electric current is passed through a mixture of fluorinatable organic starting compound and liquid anhydrous hydrogen fluoride to produce a fluorinated product. In addition to the desired perfluorochemical, however, the ECF product also contains partially-fluorinated compounds or fluorohydrochemicals, which decrease the inertness of the product and are therefore usually removed from the crude ECF reactor product by treatment with base and distillation. (See, for example, Kirk-Othmer *Encyclopedia of Chemical Technology*, Third Edition, Volume 10, pages 874–81 (especially, page 878), John Wiley & Sons, New York (1980); Moore et al., J. Fluorine Chem. 32, 41 (especially, page 60) (1986); and Nishimura et al., J. Printed Circuitry 6(4), 203 (1991).)

Inert perfluorochemicals can also be prepared by direct fluorination, in which fluorinatable organic starting compound is reacted with fluorine gas. (See, for example, U.S. Pat. No. 5,093,432 (Bierschenk et al.).) Direct fluorination, however, also produces fluorinated product which contains some partially-fluorinated compounds or fluorohydrochemicals, the removal of which is generally required (by treatment with base or with additional fluorine gas) to maximize the inertness of the product. (See, for example, International Patent Publication No. WO 90/06296 (Minnesota Mining and Manufacturing Company), especially, page 8.)

The difficulty of obtaining highly pure perfluorinated product by direct fluorination, ECF, or other fluorination methods is described in U.S. Pat. No. 4,929,317 (Nishimura et al.), which discloses a process for the preparation of perfluoro organic compounds. This process comprises a first step of gently fluorinating an organic compound having carbon-to-hydrogen bonds to form a mixture of compounds in which the ratio of the number of fluorine atoms to the number of hydrogen atoms is at least 8, and a second (purification) step of contacting the mixture with molecular fluorine at a temperature of 110° to 180° C.

U.S. Pat. No. 4,035,250 (Walters et al.) describes an electrochemical fluorination process for the production of perfluoro-n-heptane comprising cooling the effluent from a first cell to a temperature sufficient to condense such effluent, separating a fluorocarbon-rich phase from the condensate, carrying out a second stage fluorination wherein partially fluorinated n-heptanes in the fluorocarbon-rich phase are further fluorinated, and separating perfluoro-n-heptane from the second stage effluent by simple fractionation.

U.S. Pat. No. 4,029,552 (Fozzard) also discloses a process for obtaining high purity perfluoro-n-heptane from an electrochemical fluorination product by use of a novel toluene/perfluoro-n-heptane constant boiling mixture.

U.S. Pat. No. 3,737,470 (Cottle) describes a process for the separation and recovery of perhalogenated fluorocarbons, e.g., perfluorocarbons and/or chlorofluorocarbons, contained in a mixture together with partially halogenated fluorohydrocarbons, e.g., chlorofluorohydrocarbons. The process comprises dehydrohalogenating the partially halogenated fluorohydrocarbons to the corresponding olefins, halogenating the olefins to perhalogenated fluorocarbons, and fractionating the resulting mixture to separate and recover the perhalogenated fluorocarbons. The dehydrohalogenation step can be carried out using alkali metal hydroxides or solutions or dispersions thereof (see column 6, line 29, through column 7, line 30).

U.S. Pat. No. 4,618,731 (Beck) discloses a process for purifying 2-perfluoroalkylethanols by reaction of the $R_fCH_2CH_2I$ and $R_fI$ impurities with an excess of an alkali metal hydroxide (preferably sodium hydroxide, which can be aqueous, as shown in column 2, line 45) and a $C_1$–$C_3$ alcohol (preferably isopropanol) in a closed vessel at a temperature above 80° C. (preferably 100°–115° C.) until neither of the iodide impurities can be detected in the final product.

Japanese Patent Application No. 2-412800 (Tokuyama Sotatsu K. K.) describes a method of preparing perfluorinated organic compounds by fluorinating organic compound, contacting the product of the fluorination with at least one type of base selected from the group of alkali metal hydroxides, alkaline earth metal hydroxides, secondary amines, and tertiary amines, and then contacting the resulting product with molecular fluorine. The base is generally used in the form of a solution in water or alcohol, and better results are said to be obtained when the base comprises a mixture of alkali metal hydroxide or alkaline earth metal hydroxide with secondary or tertiary amine.

U.S. Pat. No. 4,766,261 (Bierl) discloses a method of purifying fluorocarbons by contacting the fluorocarbons with a substantially dry (containing no more than 30 weight percent water), strongly basic and strongly nucleophilic alkali or alkaline earth metal compound (e.g., a metal hydroxide or an inorganic or organic metal oxide), and separating the decomposition products which form. The compound may be used in the form of a solid, e.g., in pellet, powder, or flake form, or it may be dispersed or dissolved in a non-aqueous solvent such as alcohol.

Briefly, this invention provides a continuous process for the purification of perfluorochemical compositions, namely, a continuous process for the separation and, optionally, the recovery of substantially inert perfluorochemicals from the mixture of inert perfluorochemicals and isomeric fluorohydrochemicals resulting from fluorination methods such as direct fluorination or ECF. The process comprises continuously mixing a perfluorochemical composition, comprising a liquid mixture of inert perfluorochemicals (e.g., perfluoroalkanes, perfluoroethers, or perfluoroalkyl tertiary amines) and isomeric fluorohydrochemicals, with a stabilization composition comprising water-miscible alkanol and an aqueous solution of base (such as potassium hydroxide). The solution of base can be prepared by dissolving the base in an amount of water sufficient to dissolve or disperse the fluoride salt by-products of the subsequent reaction of the base with the fluorohydrochemicals in the perfluorochemical composition, in which reaction the fluorohydrochemicals are dehydrohalogenated to fluoroolefins. The amount of alkanol used is an amount greater than that which is stoichiometrically necessary to completely convert the resulting fluoroolefins to alkoxyvinyl ethers. The resulting stabilized, liquid mixture comprising the treated perfluorochemical composition can be allowed to phase-separate to form an upper aqueous, fluorohydrochemical reaction product-containing phase and a lower perfluorochemical-rich phase.

Preferably, the alkanol used in the process of the invention is an alkanol having from one to four carbon atoms (or a mixture of one or more of such alkanols) and the aqueous solution of base contains a stoichiometric excess (relative to the amount of hydrogen or "hydride" in the fluorohydrochemicals) of base selected from the group consisting of alkali metal hydroxides, oxides, and alkoxides; ammonium hydroxide; primary, secondary, and tertiary amines; and mixtures thereof. The process preferably also further comprises a step in which substantially inert perfluorochemicals are recovered from the stabilized mixture, e.g., by draining from it the resulting lower perfluorochemical-rich phase.

The continuous process of the invention is a simple, effective method of purifying perfluorochemical compositions and provides a lower-cost alternative to conventional batch processes. The process enables the removal, for example, of up to about 99 percent or more of the fluorohydrochemical component of a perfluorochemical composition, depending upon the initial fluorohydrochemical content of the composition and the reaction conditions utilized.

Perfluorochemical compositions which can be purified by the process of the invention comprise such inert perfluorochemicals as perfluoroalkanes, pentafluorosulfanyl-substituted perfluoroalkanes, perfluoroethers, perfluoroaminoethers, perfluoroalkyl tertiary amines, and mixtures thereof. The perfluorochemical compositions are generally the product of a fluorination process, e.g., electrochemical fluorination or direct fluorination, and thus typically comprise a mixture of one or more inert perfluorochemicals and one or more isomeric fluorohydrochemicals. Small amounts of fluoroolefins, unreacted organic starting compound, lower molecular weight cleavage products, and higher molecular weight coupling products may also be present in the perfluorochemical compositions. Both the perfluorochemical and the fluorohydrochemical components of the perfluorochemical compositions can have some chlorine content, that is, carbon-bonded chlorine atoms. Representative examples of suitable inert perfluorochemicals include perfluoropropane, perfluorobutane, perfluoropentane, perfluorohexane, perfluoroheptane, perfluorooctane, perfluorononane, perfluorodecane, 1,8-dichloroperfluorooctane, 1-pentafluorosulfanylperfluorobutane, 1-pentafluorosulfanylperfluoropentane, 1-pentafluorosulfanylperfluorohexane, bis(chlorobutyl)ether, perfluorobutyltetrahydrofuran, perfluoro-N-methylmorpholine, perfluoro-N-ethylmorpholine, perfluoro-N-isopropylmorpholine, perfluorotriethylamine, perfluorotripropylamine, perfluorotributylamine, perfluorotripentylamine, and mixtures thereof. The process is expecially useful for purifying $C_3$-$C_9$ perfluoroalkanes, pentafluorosulfanyl-substituted perfluoroalkanes, perfluoroethers, perfluoroaminoethers, perfluoroalkyl tertiary amines, and mixtures thereof, as the $C_3$-$C_9$ compounds form alkoxyvinyl ethers which are more soluble in aqueous alkanol (and therefore more easily separated from the inert perfluorochemical) than are the higher molecular weight compounds. Most preferably, the process is utilized to purify $C_3$-$C_6$ perfluoroalkanes, perfluoroethers, perfluoroaminoethers, perfluoroalkyl tertiary amines, and mixtures thereof.

Alkanols which are used in the process of the invention are those which have some degree of water-miscibility and generally which are capable of converting the fluoroolefin (formed in the reaction of base with the fluorohydrochemical component of the perfluorochemical composition) to alkoxyvinyl ether (or to other more highly-oxygenated compounds formed by reaction of the alkoxyvinyl ether with alkanol). Representative examples of such alkanols include methanol, ethanol, propanol, butanol, and mixtures thereof. Primary and secondary $C_1$-$C_4$ alkanols and mixtures thereof are preferred due to their greater reactivity (relative to tertiary alkanols) with fluoroolefin. Methanol is most preferred due to its low cost and its high reactivity with fluoroolefin. A stoichiometric excess of alkanol (relative to the amount of alkanol needed to completely convert the fluoroolefin to alkoxyvinyl ether), e.g., from about 1 to about 1000 moles of alkanol per mole of hydride, is utilized so that unreacted alkanol is present after the conversion of fluoroolefin to alkoxyvinyl ether. This unreacted alkanol aids in the purification process by serving to enhance the solubility of the alkoxyvinyl ether in the aqueous phase of the treated perfluorochemical composition. Preferably, the amount of alkanol utilized ranges from about 25 to about 100 moles of alkanol per mole of hydride.

Bases which are utilized in the process of the invention are generally those which are capable of dehydrohalogenating the fluorohydrochemical component of the perfluorochemical composition to form fluoroolefins. Suitable bases include ammonium hydroxide; primary, secondary, and tertiary amines; alkali metal oxides, hydroxides, and alkoxides; and mixtures thereof. Representative examples of such bases include ammonium hydroxide, methyl amine, ethyl amine, dimethyl amine, diethyl amine, trimethyl amine, triethyl amine, sodium oxide, potassium oxide, lithium oxide, sodium hydroxide, potassium hydroxide, lithium hydroxide, sodium methoxide, potassium methoxide, lithium methoxide, sodium ethoxide, potassium ethoxide, lithium ethoxide, and mixtures thereof. Preferred bases include the alkali metal hydroxides, ammonium hydroxide, and mixtures thereof, due to their low cost. Most preferred is potassium hydroxide, as it is inexpensive, readily available, and produces fluoride salts (as a by-product of the dehydrohalogenation) which are reasonably soluble in water. Base is utilized in the form of a solution in an amount of water sufficient (at the operating temperature) to dissolve or disperse the by-product fluoride salts. The use of such a quantity of water reduces or eliminates pipe clogging problems and thus facilitates continuous operation of the process. Preferably, enough water is utilized to completely dissolve the salts. Solutions of base ranging, e.g., from about 1 to about 60 weight % KOH, can be used. Preferably, a stoichiometric excess of base (relative to the amount of hydride in the fluorohydrochemicals), e.g., from about 2 to about 20 moles of base per mole of hydride, is used to enable the complete conversion of fluorohydrochemical to fluoroolefin.

The process of the invention can be carried out by continuously introducing, e.g., by pumping, a perfluorochemical composition comprising a mixture of inert perfluorochemicals and isomeric fluorohydrochemicals to an open or closed vessel (preferably, a temperature- and pressure-controlled reactor) equipped with agitation means, while also continuously introducing a stabilization composition comprising alkanol and an aqueous solution of base to the vessel. The stabilization composition can be introduced as a single stream or as separate streams of alkanol and aqueous base. The water and base can also be introduced separately, although this is not preferred. (The perfluorochemical composition can comprise crude product per se (as it is recovered or removed) from a fluorination reactor, or it can comprise crude product which has been subjected to a preliminary purification step, e.g., distillation, crystallization, or liquid-liquid extraction, to reduce the fluorohydrochemical content of the composition prior to introduction to the vessel.) The appropriate residence time of the resulting combination of perfluorochemical composition and stabilization composition in the vessel will vary depending upon the isomeric nature of the fluorohydrochemicals, the hydride content of the perfluorochemical composition, the conditions of temperature and pressure, the degree of agitation, the nature of the base, the base concentration of the stabilization composition, and the degree of product purity desired. The appropriate residence time can be determined by monitoring the hydride content of the substantially inert perfluorochemical product. Residence times of, e.g., from about 6 to about 8 hours have been found useful for perfluoroalkanes having a hydride content of from about 0.001 to about 0.1 weight percent. The vessel contents are preferably agitated to facilitate reactant contact, and the vessel can be maintained at any temperature and pressure at which the mixture of inert perfluorochemicals and isomeric fluorohydrochemicals is maintained in a liquid state and which provides a desired rate of reaction, i.e., a desired rate of conversion of fluorohydrochemical to alkoxyvinyl ether. Temperatures of, e.g., from about 0° to about 250° C. and pressures of, e.g., from about 1 to about 100 atmospheres can be used. Preferably, temperatures ranging from about 0° to about 150° C. and pressures ranging from about 1 to about 20 atmospheres are utilized.

A product-containing effluent comprising inert perfluorochemicals, water, alkanol, alkoxyvinyl ether, and any unreacted base and unreacted fluorohydrochemical can be withdrawn (continuously or semi-continuously) from the vessel. The effluent can be passed to a phase separation vessel, e.g., a decanter, where it can be allowed to phase-separate into a lower perfluorochemical-rich phase and an upper aqueous, alkoxyvinyl ether-containing phase. Preferably, substantially inert perfluorochemicals are recovered (continuously or semi-continuously), e.g., by draining the lower perfluorochemical-rich phase from either the vessel or the decanter. If desired, the substantially inert perfluorochemicals can be further purified or "polished" (to further reduce its fluorohydrochemical content), for example by such means as distillation, contacting the perfluorochemicals with fluorine gas (e.g., by bubbling fluorine gas through a liquid perfluorochemical), or subjecting the perfluorochemicals to a water wash followed by an adsorption treatment with silica gel, molecular sieves, or activated carbon.

The continuous process of the invention is useful as a simple, effective method for purifying perfluorochemical compositions comprising inert perfluorochemicals (e.g., perfluoroalkanes, perfluoroethers, and perfluoroalkyl tertiary amines) and isomeric fluorohydrochemicals. Such perfluorochemical compositions resulting from fluorination methods such as direct fluorination or ECF can be easily and effectively purified by this process at a lower cost than by conventional batch processes.

This invention is further illustrated by the following examples, but the particular materials and amounts thereof recited in these examples, as well as other conditions and details, should not be construed to unduly limit this invention.

EXAMPLES

EXAMPLE 1

Purification of a Perfluorochemical Composition Comprising Perfluoro-N-methyl Morpholine A crude perfluorochemical composition comprising perfluoro-N-methyl morpholine was prepared by electrochemical fluorination of N-methyl morpholine. The resulting reaction product (or crude composition) was fractionated using a packed column, and $^1$H NMR analysis of the fractionated material revealed 0.0047 weight percent hydride (present in the form of a random mixture of fluorohydrochemical isomers corresponding to the formula $C_5ONH_xF_{11-x}$, where $x=1-11$).

The resulting fractionated composition was pumped into a 600 mL, three-stage, temperature- and pressure-controlled, stirred tank reactor (which was equipped with a first lower inlet for introducing a stabilization composition, a second lower inlet for introducing the perfluorochemical composition, and an upper outlet for removing a product-containing effluent) at a rate of 150 g/hr (0.33 lb/hr), while concurrently a stabilization composition comprising 10% by weight KOH in a mixture of water and methanol (45 weight percent aqueous KOH diluted to 10 weight percent with methanol) was pumped into the reactor at a rate of 10 to 12 g/hr (0.022–0.026 lbs/hr). These flow rates are equivalent to 2.5 moles of KOH per mole of hydride (in the crude perfluorochemical composition) and 34.7 moles of methanol per mole of hydride. The reactor was maintained at atmospheric pressure and at a temperature of 25° C., and an agitation rate of 300 rpm was utilized. The residence time of the reactor contents was calculated to be 7 hours.

The resulting stabilized, product-containing effluent from the reactor was collected in a flask, transferred to a separatory funnel, and allowed to phase-separate into an upper aqueous phase and a lower perfluorochemical-rich phase. The lower perfluorochemical-rich phase was drained from the funnel, washed with water, and then passed through a packed column containing silica gel. $^1$H NMR analysis of the resulting recovered perfluoro-N-methyl morpholine showed 0.0023 weight percent hydride, indicating that a reduction of approximately 50 percent in the hydride content of the perfluorochemical composition had been achieved.

EXAMPLE 2

Purification of a Perfluorochemical Composition Comprising Perfluoropentane

A crude perfluorochemical composition comprising perfluoropentane was prepared by electrochemical fluorination of pentane. The resulting reaction product (or crude composition) was fractionated using a packed column, and $^1$H NMR and gas chromatographic analysis of the fractionated material revealed 0.015 weight percent hydride (present in the form of a random mixture of fluorohydrochemical isomers corresponding to the formula $C_5H_xF_{12-x}$ where $x=1-12$).

The resulting fractionated composition was pumped into a 7.6 liter (2 gallon), six-stage, temperature- and pressure-controlled, stirred tank reactor (which was equipped with a first lower inlet for introducing a stabilization composition, a second lower inlet for introducing the perfluorochemical composition, and an upper outlet for removing a product-containing effluent) at a rate of 820 g/hr (1.80 lb/hr), while concurrently a stabilization composition comprising 20% by weight KOH in a mixture of water and methanol (45 weight percent aqueous KOH diluted to 20 weight percent with methanol) was pumped into the reactor at a rate of 290 g/hr (0.64 lb/hr). The reactor was maintained at a pressure of 549 kPa (65 psig) and at a temperature of 100° C., and an agitation rate of 1000 rpm was used. The residence time of the reactor contents was calculated to be 9.7 hours.

The resulting stabilized, product-containing effluent from the reactor was collected in a jacketed vessel maintained at 15.5° C. where it immediately phase-separated into an upper aqueous phase and a lower perfluorochemical-rich phase. An aliquot of the lower perfluorochemical-rich phase was drained from the vessel, washed with water, and then passed through a packed column containing silica gel. $^1$H NMR analysis of the resulting recovered perfluoropentane showed that only 0.00047 weight percent hydride remained in the purified perfluorochemical composition.

A sample of the recovered perfluoropentane was also analyzed for residual hydride by the procedure described in Arcus et al., *Testing for Chemical Inertness in Electronic Coolants*, Int. Electronic Circuit Packaging Symposium, 10th Symposium, paper 2/4, 1969. Using this procedure, the sample was contacted with piperidine and then extracted with water. The resulting aqueous solution was then passed through an anion exchange resin to remove piperidine, and the "free fluoride" (derived from dehydrofluorination of fluorohydrocarbons) was measured using a fluoride ion-selective electrode.

A summary of the analytical results and the purification conditions is shown in Table 1.

EXAMPLE 3-5

Purification of Perfluorochemical Compositions Comprising Perfluoropentane

Other samples of the fractionated composition of Example 2 were purified in essentially the same manner as in Example 2, using the same equipment and using a stabilization composition of the same concentration, but using various different temperatures, pressures, agitation rates, feed rates, and residence times. The resulting purified samples were recovered and analyzed essentially as in Example 2. The purification conditions and the analytical results (which indicated that only very small amounts of hydride remained in the purified samples) are shown in Table 1 below.

TABLE 1

| Example No. | Agitation Rate (rpm) | Temperature (°C.) | Pressure (kPa) | Feed Rate of Perfluorochemical Composition (g/hr) | Feed Rate of Stabilization Composition (g/hr) | Residence Time (Hrs) | Final Free Fluoride (μg/g) | Final Weight % Hydride by $^1$H NMR $\times 10^{-4}$ |
|---|---|---|---|---|---|---|---|---|
| 2 | 1000 | 100 | 549 | 820 | 290 | 9.7 | 0.2 | 4.7 |
| 3 | 1000 | 100 | 549 | 1,940 | 77 | 6.1 | 0.5 | 5.2 |
| 4 | 500 | 100 | 549 | 1,990 | 82 | 6.0 | <1 | 7.4 |
| 5 | 1000 | 129 | 618 | 1,820 | 145 | 6.2 | 1.8 | 6.3 |

EXAMPLE 6

Purification of a Perfluorochemical Composition Comprising Perfluorohexane

A crude perfluorochemical composition comprising perfluorohexane was prepared by electrochemical fluorination of hexane. The resulting reaction product (or crude composition) was fractionated using a packed column, and $^1$H NMR and gas chromatographic analysis of the fractionated material revealed 0.0024 weight percent hydride (present in the form of a random mixture of fluorohydrochemical isomers corresponding to the formula $C_6H_xF_{14-x}$ where $x=1-14$).

The resulting fractionated composition was pumped into the 7.6 liter (2 gallon) reactor described in Example 2 at a rate of 660 g/hr (1.45 lb/hr), while concurrently a stabilization composition comprising 20% by weight KOH in a mixture of water and methanol (45 weight percent aqueous KOH diluted to 20 weight percent with methanol) was pumped into the reactor at a rate of 36 g/hr (0.08 lb/hr). The reactor was maintained at a pressure of 418 kPa (46 psig) and at a temperature of 100° C. and an agitation rate of 1000 rpm was used. The residence time of the reactor contents was calculated to be 17.7 hours.

The resulting stabilized, product-containing effluent from the reactor was collected in a jacketed vessel maintained at 15.5° C., where it immediately phase-separated into an upper aqueous phase and a lower perfluorochemical-rich phase. An aliquot of the lower perfluorochemical-rich phase was drained from the vessel, washed with water, and then passed through a packed column containing silica gel. A sample of the resulting recovered perfluorohexane was analyzed essentially as in Example 2. The results are shown in Table 2 and indicate that only a very small amount of hydride (0.000019 weight percent) remained in the purified perfluorochemical composition.

EXAMPLE 7-9

Purification of Perfluorochemical Compositions Comprising Perfluorohexane

Other samples of the fractionated composition of Example 6 were purified in essentially the same manner as in Example 6, using the same equipment and agitation rate, but using various different temperatures, pressures, feed rates, stabilization composition concentrations, and residence times. The resulting purified samples were recovered and analyzed essentially as in Example 6. The purification conditions and the analytical results (which indicated that only very small amounts of hydride remained in the purified samples) are shown in Table 2 below.

TABLE 2

| Example No. | Agitation Rate (rpm) | Temperature (°C.) | Pressure (kPa) | Feed Rate of Perfluorochemical Composition (g/hr) | Feed Rate of Stabilization Composition (g/hr) | Concentration of Stabilization Composition* (weight % KOH in water/methanol) | Residence Time (Hrs) | Final Free Fluoride (μg/g) | Final Weight % Hydride by $^1$H NMR ($\times 10^{-5}$) |
|---|---|---|---|---|---|---|---|---|---|
| 6 | 1000 | 100 | 418 | 660 | 36 | 20 | 17.7 | 1.5 | 1.9 |
| 7 | 1000 | 100 | 480 | 590 | 41 | 20 | 19.3 | 1.5 | 1.9 |
| 8 | 1000 | 100 | 446 | 510 | 268 | 12.9 | 13.2 | 0.02 | 1.2 |
| 9 | 1000 | 100 | 446 | 1,160 | 268 | 12.9 | 7.9 | 0.01 | 2.4 |

*Prepared by diluting 45 weight % acqueous KOH with methanol.

Various modifications and alterations of this invention will become apparent to those skilled in the art without departing from the scope and spirit of this invention.

We claim:

1. A process for purifying a perfluorochemical composition which comprises continuously mixing said perfluorochemical composition, comprising a liquid mixture of inert perfluorochemicals and isomeric fluorohydrochemicals, with a stabilization composition comprising water-miscible alkanol and an aqueous solution of base made by dissolving said base in an amount of water sufficient to dissolve or disperse the fluoride salt by-products of the reaction of said base with said fluorohydrochemicals to form fluoroolefins, the amount of said alkanol in said stabilization composition being in stoichiometric excess of the amount needed to completely convert said fluoroolefins to alkoxyvinyl ethers.

2. The process of claim 1 further comprising a step of recovering substantially inert perfluorochemicals from the resulting stabilized composition.

3. The process of claim 1 wherein said perfluorochemical composition comprises crude product from a fluorination reactor.

4. The process of claim 3 wherein said perfluorochemical composition has been subjected to a preliminary purification step to reduce the fluorohydrochemical content of said composition.

5. The process of claim 4 wherein said preliminary purification step is distillation.

6. The process of claim 1 wherein said alkanol is selected from the group consisting of $C_1$–$C_4$ alkanols and mixtures thereof.

7. The process of claim 6 wherein said alkanol is selected from the group consisting of primary and secondary $C_1$–$C_4$ alkanols and mixtures thereof.

8. The process of claim 7 wherein said alkanol is methanol.

9. The process of claim 1 wherein said aqueous solution of base contains an amount of said base which is in stoichiometric excess of the amount of hydride in said fluorohydrochemicals.

10. The process of claim 1 wherein said aqueous solution of base contains an amount of water sufficient to dissolve said fluoride salt by-products.

11. The process of claim 1 wherein said base is selected from the group consisting of ammonium hydroxide; primary, secondary, and tertiary amines; and alkali metal oxides, hydroxides, and alkoxides; or mixtures thereof.

12. The process of claim 11 wherein said base is selected from the group consisting of alkali metal hydroxides, and ammonium hydroxide, or mixtures thereof.

13. The process of claim 12 wherein said base is potassium hydroxide.

14. The process of claim 1 wherein said inert perfluorochemicals are selected from the group consisting of perfluoroalkanes, perfluorosulfanyl-substituted perfluoroalkanes, perfluoroethers, perfluoroaminoethers, and perfluoroalkyl tertiary amines, or mixtures thereof.

15. The process of claim 14 wherein said inert perfluorochemicals are selected from the group consisting of $C_3$–$C_9$ perfluoroalkanes, $C_3$–$C_9$ perfluorosulfanyl-substituted perfluoroalkanes, $C_3$–$C_9$ perfluoroethers, $C_3$–$C_9$ perfluoroaminoethers, and $C_3$–$C_9$ perfluoroalkyl tertiary amines, or mixtures thereof.

16. The process of claim 15 wherein said inert perfluorochemicals are selected from the group consisting of $C_3$–$C_6$ perfluoroalkanes, $C_3$–$C_6$ perfluoroethers, $C_3$–$C_6$ perfluoroaminoethers, and $C_3$–$C_6$ perfluoroalkyl tertiary amines, or mixtures thereof.

17. A process for purifying a perfluorochemical composition which comprises (a) continuously mixing said perfluorochemical composition, comprising a mixture of (i) inert perfluorochemicals selected from the group consisting of $C_3$–$C_6$ perfluoroalkanes, $C_3$–$C_6$ perfluoroethers, $C_3$–$C_6$ perfluoroaminoethers, and $C_3$–$C_6$ perfluoroalkyl tertiary amines, or mixtures thereof, and (ii) isomeric fluorohydrochemicals, with a stabilization composition comprising methanol and an aqueous solution of potassium hydroxide made by dissolving said potassium hydroxide in an amount of water sufficient to dissolve the fluoride salt by-products of the reaction of said potassium hydroxide with said fluorohydrochemicals to form fluoroolefins, the amount of said potassium hydroxide in said aqueous solution being in stoichiometric excess of the amount of hydride in said fluorohydrochemicals, and the amount of said methanol in said stabilization composition being in stoichiometric excess of the amount needed to completely convert said fluoroolefins to alkoxyvinyl ethers; and (b) recovering substantially inert perfluorochemicals from the resulting stabilized composition.

18. The process of claim 17 wherein said perfluorochemical composition comprises crude product from a fluorination reactor.

19. The process of claim 18 wherein said perfluorochemical composition has been subjected to a preliminary distillation step to reduce the fluorohydrochemical content of said composition.

20. The process of claim 17 further comprising the steps of subjecting the resulting recovered substantially inert perfluorochemicals to a water wash and a silica gel treatment.

* * * * *